(12) United States Patent
Mou et al.

(10) Patent No.: US 11,255,322 B2
(45) Date of Patent: Feb. 22, 2022

(54) ELECTRONIC DEVICE WITH ACTUATING AND SENSING MODULE

(71) Applicant: Microjet Technology Co., Ltd., Hsinchu (TW)

(72) Inventors: Hao-Jan Mou, Hsinchu (TW); Ta-Wei Hsueh, Hsinchu (TW); Shih-Chang Chen, Hsinchu (TW); Li-Pang Mo, Hsinchu (TW); Chi-Feng Huang, Hsinchu (TW); Yung-Lung Han, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 728 days.

(21) Appl. No.: 16/012,471

(22) Filed: Jun. 19, 2018

(65) Prior Publication Data
US 2019/0011392 A1 Jan. 10, 2019

(30) Foreign Application Priority Data
Jul. 10, 2017 (TW) .................................. 106123107

(51) Int. Cl.
*G01N 27/404* (2006.01)
*G01N 27/407* (2006.01)
(Continued)

(52) U.S. Cl.
CPC ......... *F04B 43/046* (2013.01); *G01N 27/407* (2013.01); *G01N 27/4045* (2013.01);
(Continued)

(58) Field of Classification Search
CPC ............ G01N 27/4045; G01N 27/407; G01N 33/0022; G01N 33/0031; F04B 43/046;
(Continued)

(56) References Cited

U.S. PATENT DOCUMENTS

| 6,165,347 A | 12/2000 | Warburton |
| 2010/0229658 A1 | 9/2010 | Glezer et al. |

(Continued)

FOREIGN PATENT DOCUMENTS

| CN | 235754850 U | 11/2016 |
| EP | 2 733 484 A1 | 5/2014 |

(Continued)

OTHER PUBLICATIONS

Extended European Search Report, dated Oct. 19, 2018, for European Application No. 18178540.3.
(Continued)

*Primary Examiner* — Dennis White
(74) *Attorney, Agent, or Firm* — Birch, Stewart, Kolasch & Birch, LLP

(57) ABSTRACT

An electronic device includes a casing, a speaker enclosure and an actuating and sensing module. The casing has an opening. The speaker enclosure is disposed within the casing to enclose a speaker, in communication with the opening of the casing and divided into a first speaker compartment and a second speaker compartment by a partition plate disposed corresponding to the opening, so that the opening of the casing is in communication with the first speaker compartment and the second speaker compartment. The actuating and sensing module is disposed within the first speaker compartment. The speaker is disposed within the second speaker compartment. The actuating and sensing module comprises a fluid transportation device and a sensor. The fluid transportation device is driven to transport a fluid from outside the casing into the first speaker compartment through the opening of the casing to make the fluid sensed by the sensor.

20 Claims, 12 Drawing Sheets

(51) Int. Cl.
*G01N 33/00* (2006.01)
*F04B 43/04* (2006.01)
*H04R 1/02* (2006.01)
*H04M 1/03* (2006.01)
*G06F 1/16* (2006.01)

(52) U.S. Cl.
CPC ..... *G01N 33/0022* (2013.01); *G01N 33/0031* (2013.01); *G06F 1/16* (2013.01); *H04M 1/035* (2013.01); *H04R 1/028* (2013.01); *H04M 2250/12* (2013.01); *H04R 2499/11* (2013.01)

(58) Field of Classification Search
CPC ..... H04M 1/035; H04M 2250/12; G06F 1/16; H04R 1/028; H04R 2499/11
See application file for complete search history.

(56) References Cited

U.S. PATENT DOCUMENTS

2014/0377099 A1 12/2014 Hsueh et al.
2015/0219608 A1* 8/2015 Choi ................ G06F 3/017
                                                        73/23.2
2016/0171869 A1 6/2016 Gullbrard et al.
2016/0353186 A1 12/2016 Rothkopf

FOREIGN PATENT DOCUMENTS

| EP | 2905673 A2 | 8/2015 |
| EP | 2 998 582 A1 | 3/2016 |
| JP | 2009-293566 A | 12/2009 |
| TW | M525446 U | 7/2016 |
| TW | M541542 U | 5/2017 |
| TW | M544653 U | 7/2017 |

OTHER PUBLICATIONS

Lu, "Smaller than rice grains, "multi-sensor integrated single chip" led the Taiwan IC industry to catch up with the Internet of Things boom", <http://technews.tw/2015/03/24/multisensor-soc-made-by-narlabs/>, total of 4 pages.

Tseng et al., "Sensor Fusion is becoming a hot trend, Smart sensor integration technology is popular", <http://www.2cm.com.tw/technologyshow_content.asp?sn=1707060005>, total of 14 pages.

* cited by examiner

ELECTRONIC DEVICE WITH ACTUATING AND SENSING MODULE

FIELD OF THE INVENTION

The present disclosure relates to an electronic device, and more particularly to an electronic device with an actuating and sensing module.

BACKGROUND OF THE INVENTION

Nowadays, people pay much attention to the devices and methods of monitoring the air quality in the environment. For example, it is important to monitor carbon monoxide, carbon dioxide, volatile organic compounds (VOC), PM2.5, and so on. The exposures of these substances in the environment will cause human health problems or even harm the life. Therefore, it is important for every country to develop and implement the environmental monitoring technology.

As known, portable electronic devices are widely used and applied in the modern lives. In addition, the portable electronic devices are indispensable electronic devices. In other words, it is feasible to use the portable electronic device to monitor the ambient air. If the portable electronic device is capable of immediately providing the monitored information to prompt the people in the environment, the people in the environment can prevent or escape immediately. Under this circumstance, the influence and injury of the gas exposure to the health will be largely reduced. In other words, the portable electronic device is suitably used for monitoring the ambient air in the environment.

Although it is obviously beneficial to make the portable electronic device equipped with environmental sensor for collecting environment data, however, when the environmental sensor is integrated into the electronic device, the monitoring sensitivity and the precision of the environmental sensor are usually not satisfied. For increasing the monitoring sensitivity and the precision of the environmental sensor, the following factors should be taken into consideration.

Firstly, the location of the environmental sensor has to be taken into consideration. The environmental sensor has to be positioned where the environmental sensor can be sensitive enough to the ambient air, e.g., an exposed outer portion of the electronic device. However, the environmental sensor disposed on the exposed outer portion is easily collided by the foreign matter and suffered from damage.

Secondly, the precision of disposition has to be taken into consideration. If the environmental sensor is deeply embedded within the electronic device, the environmental sensor not only occupies the limited space inside the electronic device, but also is interfered by the fluid and the temperature within the electronic device. Under this circumstance, the environmental sensor fails to accurately sense the surroundings of the electronic device.

Thirdly, the monitoring stability and the response time of the environmental sensor have to be taken into consideration. If the environmental sensor is deeply embedded within the electronic device, the environmental sensor is in contact with the air circulating from the outside and transferred by naturally occurring convection in the surroundings. In other words, the environmental sensor fails to fetch a consistent airflow to maintain stably monitoring. Since it is difficult to trigger response action of the environmental sensor by the circulating air transferred by convection, the response time of the environmental sensor is long and real-time monitoring is not achieved.

Therefore, there is a need of providing a technology of integrating an environmental sensor into an electronic device while increasing the monitoring accuracy and reducing response time of the environmental sensor.

SUMMARY OF THE INVENTION

An object of the present disclosure provides an electronic device with an actuating and sensing module. The actuating and sensing module is a modular structure of a sensor and a fluid transportation device. The sensor is disposed within a speaker enclosure of the electronic device to directly monitor the fluid in the environment of the present disclosure. The speaker enclosure is divided into a first speaker compartment and a second speaker compartment by a partition plate. The fluid is pumped and introduced into the first speaker compartment of the speaker enclosure and guided to the sensor by the fluid transportation device at a stable flowrate. Since the fluid is guided to the sensor at the stable flowrate, the sensor can monitor the fluid to acquire the accurate result. Moreover, since the response time of the sensor is reduced, the efficiency of monitoring the fluid is enhanced. Since the speaker is accommodated within the second speaker compartment of the speaker enclosure, the sound quality of the speaker is not interfered by the sensor and the fluid transportation device. Since the sensor is protected by the casing of the electronic device, the sensor is not readily collided by the foreign matter and suffered from damage. Moreover, since the sensing result of the sensor is not interfered by the fluid and the temperature within the electronic device, the accuracy of the sensor is enhanced.

In accordance with an aspect of the present disclosure, an electronic device is provided. The electronic device includes a casing, a speaker enclosure and an actuating and sensing module. The casing has an opening. The speaker enclosure is disposed within the casing to enclose a speaker. The speaker enclosure is in communication with the opening of the casing and divided into a first speaker compartment and a second speaker compartment by a partition plate disposed corresponding to the opening of the casing, so that the opening of the casing is in communication with the first speaker compartment and the second speaker compartment respectively. The actuating and sensing module is disposed within the first speaker compartment. The speaker is disposed within the second speaker compartment. The actuating and sensing module comprises a fluid transportation device and a sensor. The fluid transportation device is driven to transport a fluid from outside the casing into the first speaker compartment through the opening of the casing to make the fluid sensed by the sensor.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

Figure 1:
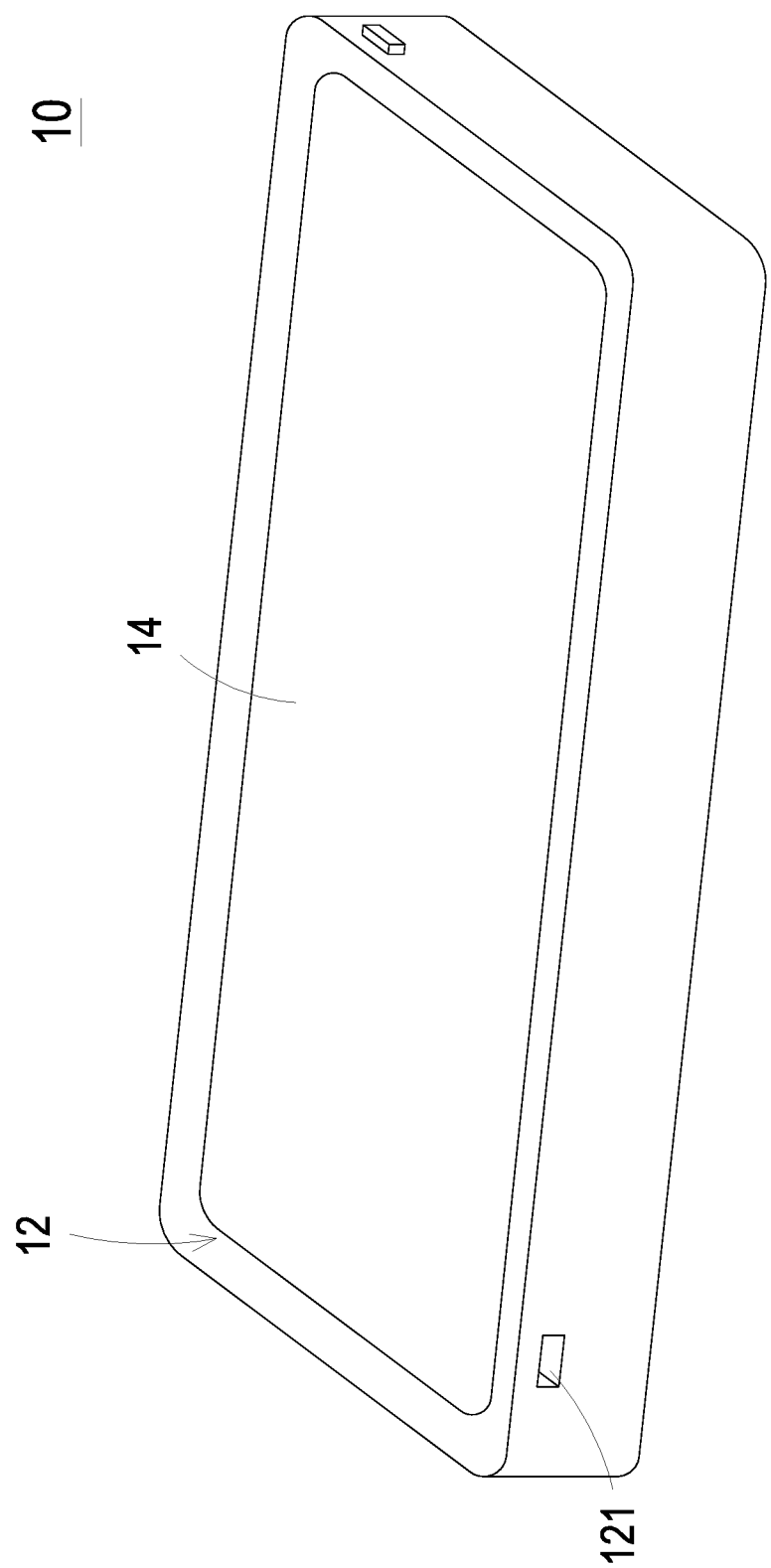
FIG. 1 is a schematic perspective view illustrating the outer appearance of an electronic device with an actuating and sensing module according to an embodiment of the present disclosure.

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

The present disclosure provides an electronic device with an actuating and sensing module. An example of the electronic device includes but is not limited to a computing device (e.g., a laptop computer, a computer monitor including an embedded computer or a tablet computer), a cellular phone, a media player, a handheld, portable or wearable electronic device (e.g., a wristwatch device, a pendent device, a headphone or earpiece device, a device embedded in the eyeglasses or other device worn on the user's head, or any other appropriate wearable small-sized device), a television, a computer monitor without the embedded computer, a game console, a navigation device, an embedded system comprising electronic equipment disposed in a touch query one machine or a vehicle, a device with the functions of two or more than two of the above electronic device, or any other appropriate electronic device.

Please refer to FIG. 1 and FIGS. 2A, 2B, 2C and 2D. The present discourse provides an electronic device 10 including at least one casing 12, at least one opening 121, at least one speaker enclosure 16b, at least one partition 161, at least one actuating and sensing module, and at least one speaker 30. The actuating and sensing module includes at least one sensor 11 and at least one fluid transportation device 13 which are combined together. The fluid transportation device 13 is driven to transport at least one fluid. The number of the casing 12, the opening 121, the speaker enclosure 16b, the partition 161, the speaker 30, the sensor 11, the fluid transportation device 13 and the fluid is exemplified by one for each in the following embodiments but not limited thereto. It is noted that each of the casing 12, the opening 121, the speaker enclosure 16b, the partition 161, the speaker 30, the sensor 11, the fluid transportation device 13 and the fluid can also be provided in plural numbers.

Figure 2A:
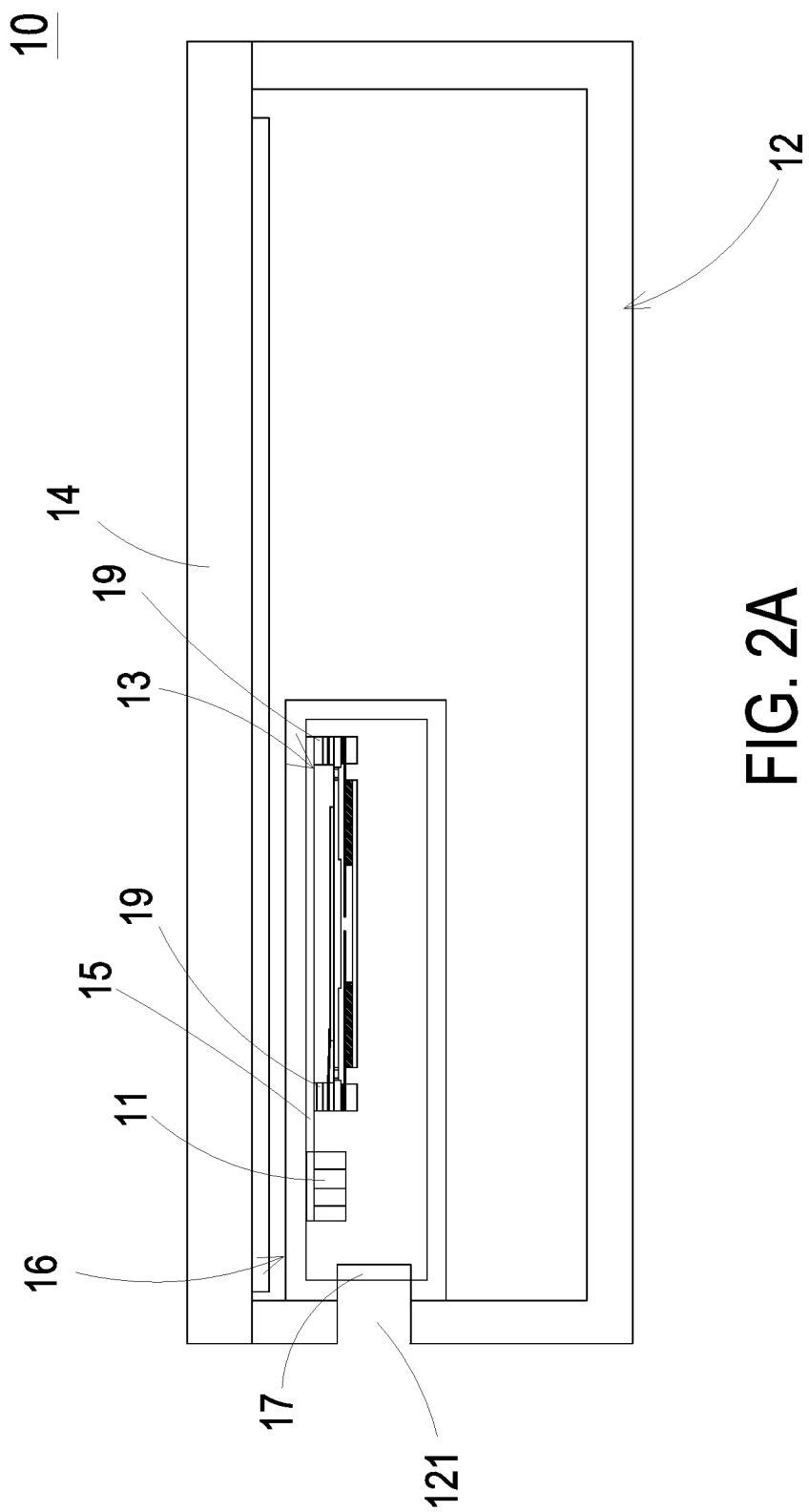
FIG. 2A is a schematic cross-sectional view illustrating the inner structure of a first exemplary electronic device of the present disclosure.

Please refer to FIG. 1 and FIG. 2A. FIG. 1 is a schematic perspective view illustrating the outer appearance of an electronic device with an actuating and sensing module according to an embodiment of the present disclosure. FIG. 2A is a schematic cross-sectional view illustrating the inner structure of a first exemplary electronic device of the present disclosure. In this embodiment, the electronic device 10 comprises a casing 12, a compartment 16 and at least one actuating and sensing module which includes a sensor 11 and a fluid transportation device 13. The sensor 11 may be an environmental sensor for sensing environmental data. The casing 12 may be made of a plastic material, a glass material, a ceramic material, a fiber composite material, a metallic material (e.g., stainless steel, aluminum, titanium, gold, etc.), any other appropriate material, or a combination of at least two above-mentioned materials. In an embodiment, the casing 12 is partially or completely composed of plural unit structures, each of which is made by a machining process or a molding process. Alternatively, in another embodiment, the casing 12 is composed of plural different structures such as an inner frame structure with one or more structure that composes the outer surface of the casing. In an embodiment, the casing 12 of the electronic device 10 comprises at least one opening 121. For example, the opening 121 is in communication with the compartment 16 for allowing the ambient fluid to be introduced into the compartment 16 through the opening 121. Optionally, the one opening 121 is serving as an audio port (e.g., the port of a speaker and/or a microphone).

The electronic device 10 further comprises a display device 14. The display device 14 is disposed within the casing 12. For example, the display device 14 is a touch screen comprising conductive capacitive touch sensor electrodes or other touch sensor components (e.g., resistive touch sensor components, acoustic touch sensor components, force-based touch sensor components, light-based touch sensor components, etc.), or the display device 14 is a non-touch screen. The capacitive touch screen electrodes may be formed of an array of indium tin oxide liners or other transparent conductive structures. Moreover, the display device 14 may be composed of a LCD pixel array, an electrophoretic pixel array, a plasma pixel array, an organic light emitting diode pixel array, a light emitting diode array, an electrowetting pixel array or any other pixel array. Moreover, the display device 14 further comprises a covering layer for achieving the protecting purpose. For example, the covering layer is a transparent glass layer, a clear plastic layer, a sapphire layer or any other transparent material layer. The covering layer is a flat layer or a curvy layer. The covering layer has a rectangular shape, a circular shape or any other appropriate shape. The material and type of the covering layer may be varied according to the practical requirements.

In accordance with a feature of the present disclosure, the electronic device 10 has an inner space, and the compartment 16 is separated and independent from the inner space of the electronic device 10. That is, the sensor 11 is protected by the casing 12 of the electronic device 10, and the sensor 11 is not readily collided by the foreign matter and suffered from damage. Moreover, since the sensing result of the sensor 11 is not interfered by the fluid and the temperature within the electronic device 10, the accuracy of the sensor 11 is enhanced. The compartment 16 is in communication with the opening 121 of the casing 12. Consequently, the fluid in the environment of the electronic device 10 can be introduced into the compartment 16 through the opening 121. For example, the fluid is a gas (e.g., air) or a liquid. The at least one actuating and sensing module is disposed within the compartment 16. That is, the sensor 11 and the fluid transportation device 13 are disposed within the compartment 16. When the fluid transportation device 13 is enabled, the fluid in the environment of the electronic device 10 is pumped into the compartment 16 through the opening 121. Consequently, the fluid within the compartment 16 is compressed and the pressure of the fluid within the compartment 16 is changed. Since the fluid is fed into the compartment 16 at a stable flowrate by the fluid transportation device 13, the sensor 11 can monitor the fluid to acquire the accurate sensing results and the response time of the sensor 11 is shortened. Preferably but not exclusively, the fluid transportation device 13 is a piezoelectric pump or a micro-electromechanical system (MEMS) pump.

Figure 2B:
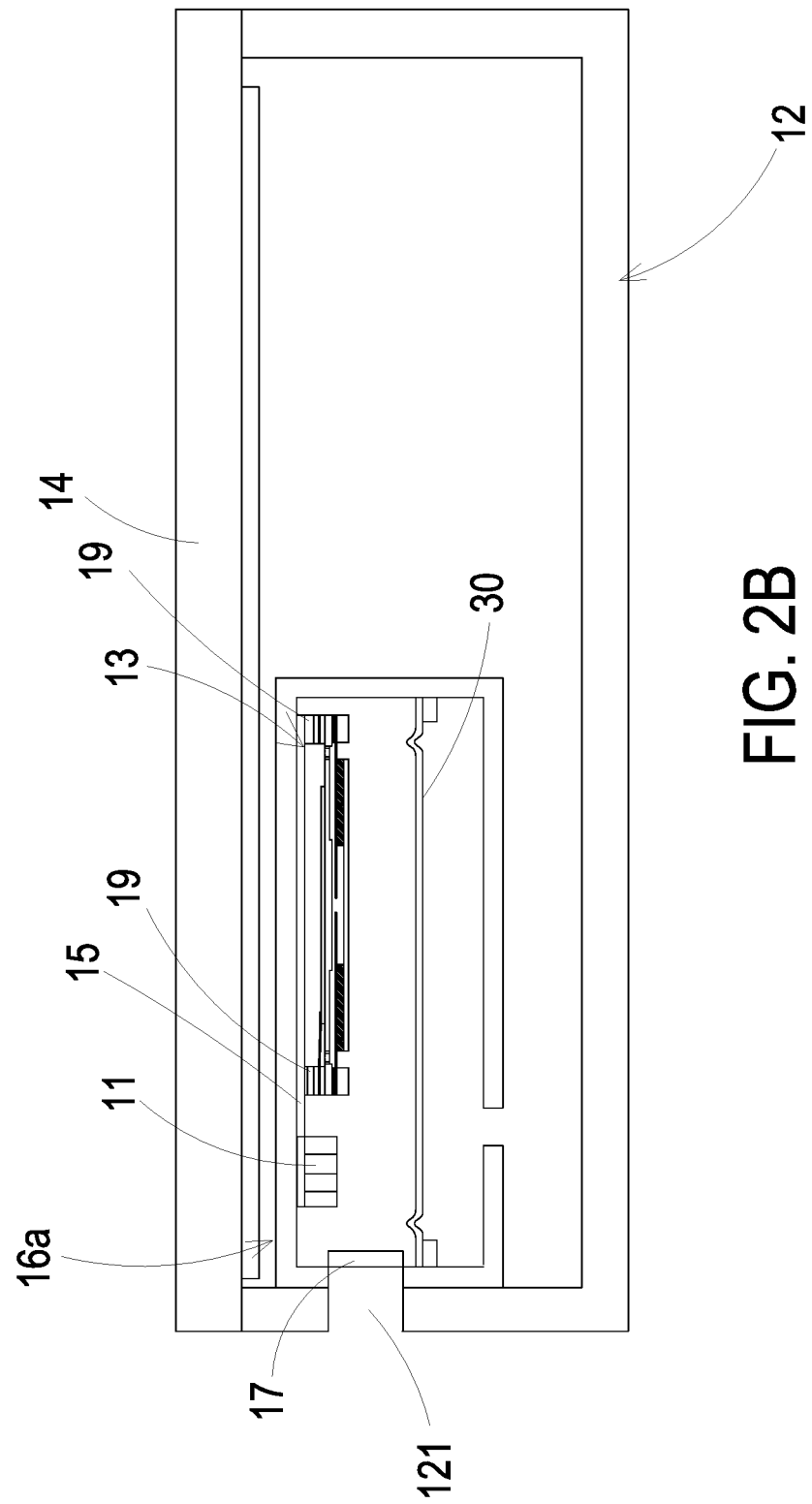
FIG. 2B is a schematic cross-sectional view illustrating the inner structure of a second exemplary electronic device of the present disclosure.

FIG. 2B is a schematic cross-sectional view illustrating the inner structure of a second exemplary electronic device of the present disclosure. In comparison with FIG. 2A, the opening 121 of the casing 12 of the electronic device 10' is used as an audio port and a speaker enclosure 16a of the electronic device 10' has a structure serving as the compartment 16 in FIG. 2A, in which the speaker enclosure 16a is widely used in general handheld or portable electronic device. The speaker enclosure 16a is disposed within the casing 12 to enclose a speaker 30 and is in communication with the opening 121. A diaphragm of the speaker 30 is disposed across the inner space of the speaker enclosure 16a, so that the speaker enclosure 16a is separated and independent from the inner space of the electronic device 10', and the sensor 11 and the fluid transportation device 13 are disposed within the speaker enclosure 16a. When the fluid transportation device 13 is enabled, the fluid in the environment of the electronic device 10' is pumped into the speaker enclosure 16a through the opening 121. Consequently, the fluid within the speaker enclosure 16a is compressed and the pressure of the fluid within the speaker enclosure 16a is changed. Since the fluid is fed into the speaker enclosure 16a at a stable flowrate by the fluid transportation device 13, the sensor 11 can monitor the fluid to acquire the accurate sensing results and the response time of the sensor 11 is reduced.

Figure 2C:
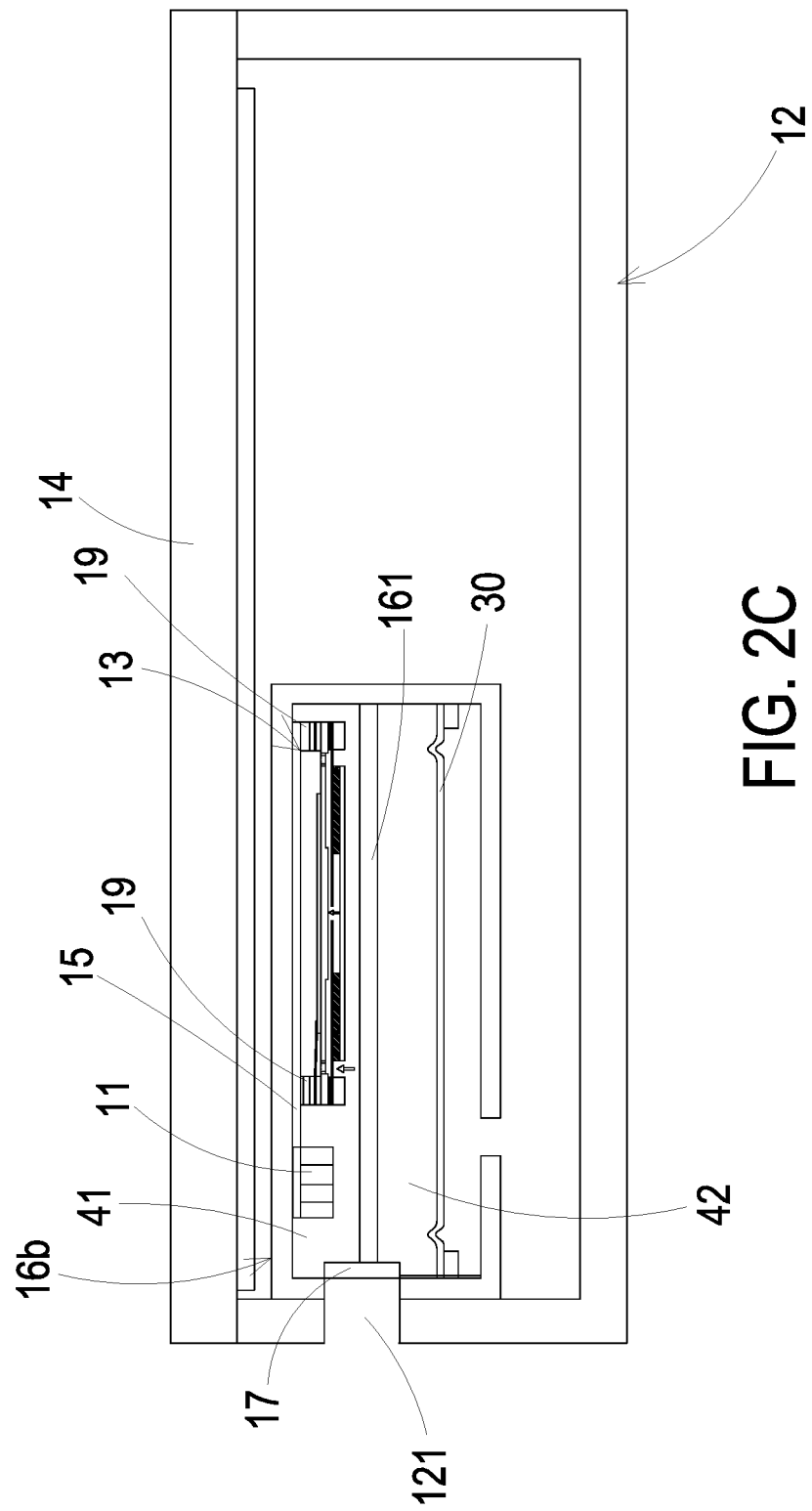
FIG. 2C is a schematic cross-sectional view illustrating the inner structure of a third exemplary electronic device of the present disclosure.

FIG. 2C is a schematic cross-sectional view illustrating the inner structure of a third exemplary electronic device of the present disclosure. In comparison with FIG. 2A, the opening 121 of the casing 12 of the electronic device 10" is used as an audio port and a speaker enclosure 16b of the electronic device 10" has a structure serving as the compartment 16 in FIG. 2A, in which the speaker enclosure 16b is widely used in general handheld or portable electronic device. The speaker enclosure 16b is disposed within the casing 12 to enclose a speaker 30 and is in communication with the opening 121. A diaphragm of the speaker 30 is disposed across the internal space of the speaker enclosure 16b, so that the speaker enclosure 16b is separated and independent from the inner space of the electronic device 10", and the sensor 11 and the fluid transportation device 13 are disposed within the speaker enclosure 16b. Furthermore, in this embodiment, the electronic device 10" comprises a partition plate 161 disposed corresponding to the opening 121. Due to the partition plate 161, the speaker enclosure 16b is divided into a first speaker compartment 41 and a second speaker compartment 42. The first speaker compartment 41 is serving as the compartment 16 in FIG. 2A. The second speaker compartment 42 is located under the first speaker compartment 41 for containing the speaker 30. The opening 121 is in communication with both the first speaker compartment 41 and the second speaker compartment 42. Since the speaker 30 is accommodated within the second speaker compartment 42 which is isolated from the first speaker compartment 41, the sound quality of the speaker 30 is not interfered by the sensor 11 and the fluid transportation device 13. Moreover, the sound generated by the speaker 30 is outputted from the opening 121 (i.e., the audio port). When the fluid transportation device 13 is enabled, the fluid in the environment of the electronic device 10" is pumped into the speaker enclosure 16b through the opening 121. Consequently, the fluid within the speaker enclosure 16b is compressed and the pressure of the fluid within the speaker enclosure 16b is changed. Since the fluid is fed into the speaker enclosure 16b at a stable flowrate by the fluid transportation device 13, the sensor 11 can monitor the fluid to acquire the accurate sensing results and the response time of the sensor 11 is reduced.

In the above embodiments, the electronic device 10, 10' and/or 10" may further comprise a porous material structure 17. The junction between the opening 121 and the compartment 16 and/or the junction between the opening 121 and the speaker enclosure 16a, 16b are sheltered by the porous material structure 17. For example, the porous material structure 17 is a plastic layer or a metal layer with micro perforations, an open-cell foam layer or a mesh layer. The porous material structure 17 is used for preventing the dust or other contaminate from entering the compartment 16 and/or the speaker enclosure 16a, 16b.

Figure 3:
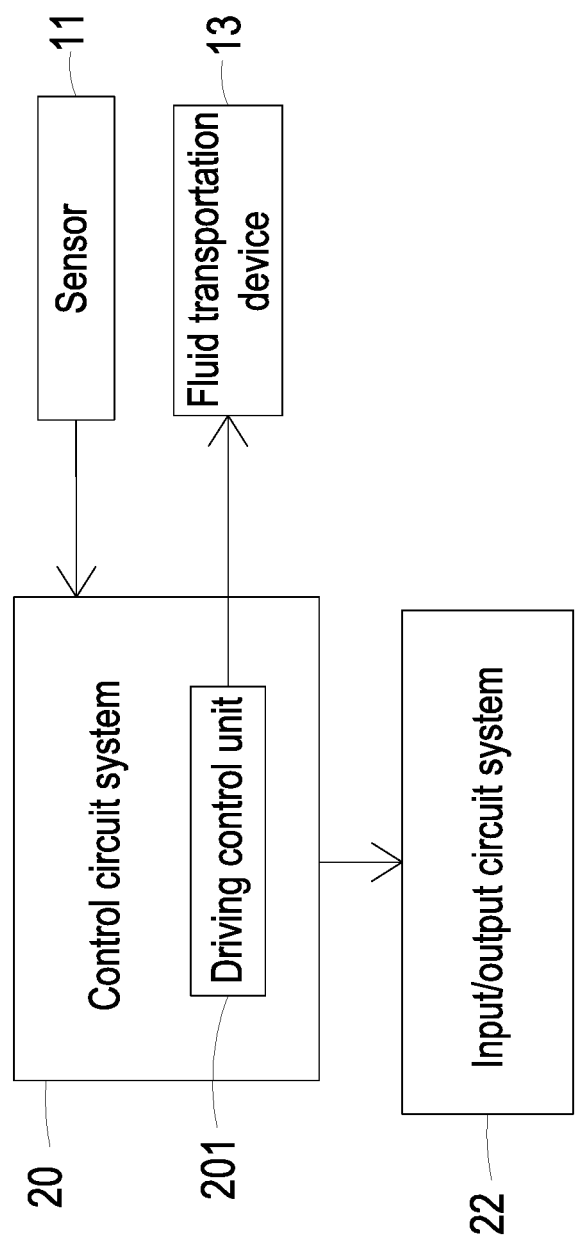
FIG. 3 is a schematic functional block diagram illustrating the architecture of the electronic device according to the embodiment of the present disclosure.

FIG. 3 is a schematic functional block diagram illustrating the architecture of the electronic device according to the embodiment of the present disclosure. The electronic device 10 further comprises a control circuit system 20 and an input/output circuit system 22. The control circuit system 20 comprises a storing unit and a processing circuit for supporting the operations of the electronic device 10. Preferably but not exclusively, the storing unit is a hard disc storage device, a non-volatile memory (e.g., a flash memory of a solid state drive or an electrically programmable read-only memory), a volatile memory (e.g., a static random access memory or a dynamic random access memory), and so on. The processing circuit of the control circuit system 20 is used for controlling the operations of the electronic device 10. In an embodiment, the processing circuit comprises one or more microprocessors, a microcontroller, a digital signal processor, a baseband processor, a power management unit, an audio chip, an application-specific integrated circuit (ASIC), and so on. The control circuit system 20 is operated when a software (e.g., an operating system program code and an application program) is executed in the electronic device 10. During the operation of the electronic device 10, the software of the control circuit system 20 is executed in the electronic device 10 to collect the sensed data from the sensor 11 of the electronic device 10. Optionally, in response to the monitored data and associated information from the sensor 11, the input/output circuit system 22 may issue a prompt message and take a proper action. For example, the prompt message is shown on the display device 14. Alternatively, the prompt message is a vibration message from a vibrator. Alternatively, the prompt message is an audible message from the speaker or any other audio output device. Alternatively, the prompt message is a patterned light with a prompt color or intensity from a light emitting diode or a light emitting diode group. Alternatively, the prompt message is any other appropriate message signal that prompts and notifies the user about the environment condition. The generation of the prompt message can remind user of danger to increase the use safety, provides the health care information to the user, provides the weather information or notifies the user about the information other than the monitored data of the sensor. The way of generating the prompt message and the content of the prompt message may be varied according to the practical requirements. The control circuit system 20 further comprises a driving control unit 201. The driving control unit 201 is electrically connected with the fluid transportation device 13 to control the operations of the fluid transportation device 13.

The data may be inputted into the electronic device 10 and outputted from the electronic device 10 through the input/output circuit system 22. Preferably but not exclusively, the input/output circuit system 22 comprises a button, a joystick, a scroll wheel, a trackpad, a keypad, a keyboard, a microphone, a speaker, a tone generator, a vibrator, a video camera, a sensor (e.g., an ambient light sensor, a proximity sensor, a magnetic sensor, a force sensor, a touch sensor, an accelerometer or any other appropriate sensor), a light emitting diode, a status indicator, a data port, and so on. The command for controlling the electronic device 10 may be inputted into the electronic device 10 through the input/output circuit system 22. Moreover, the status information of the electronic device 10 may be outputted to the input/output circuit system 22.

An example of the sensor 11 includes but is not limited to a temperature sensor, a volatile organic compound sensor, a particulate sensor, a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, or the combination thereof.

Figure 2D:
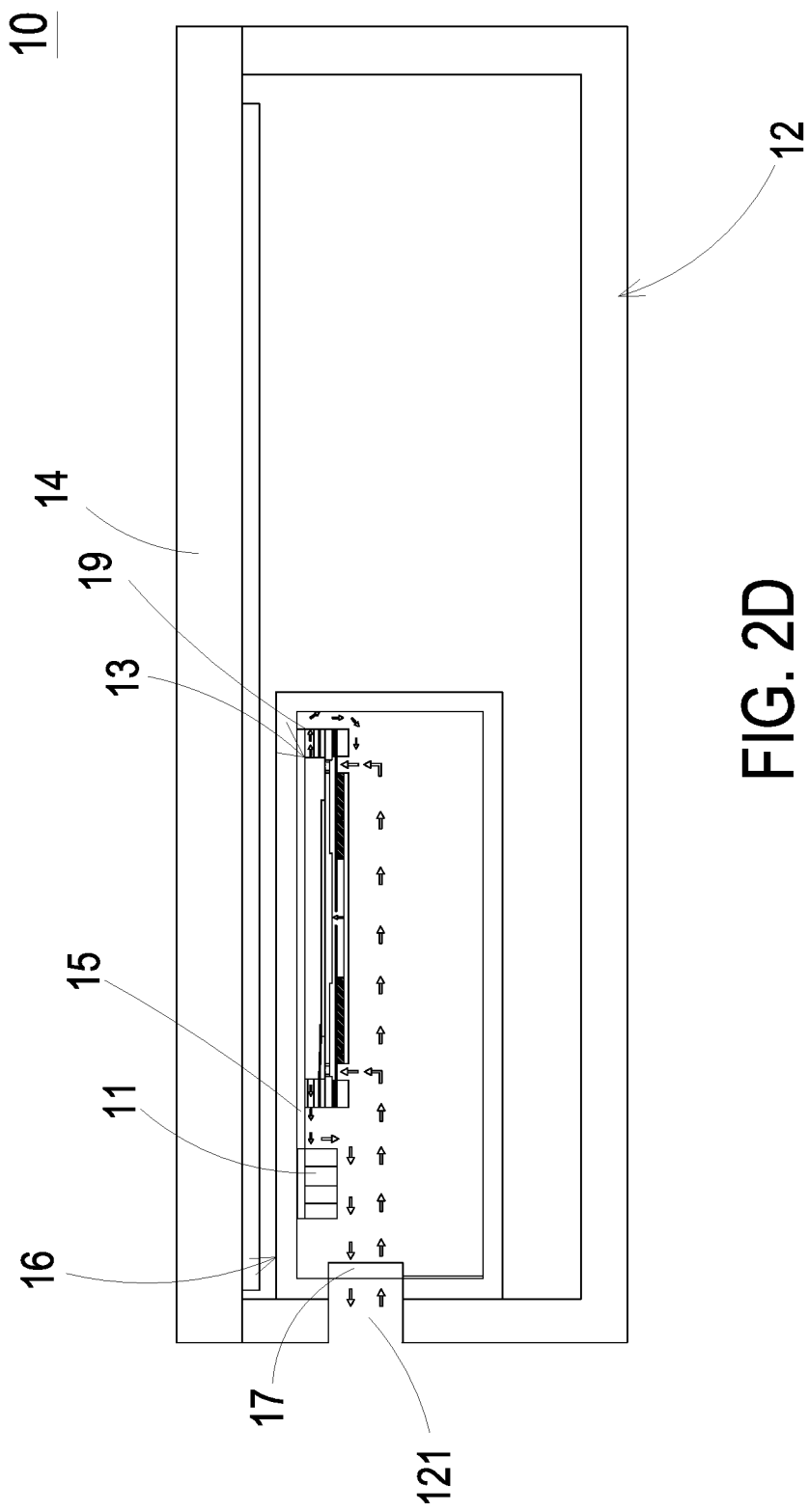
FIG. 2D is a schematic cross-sectional view illustrating the actions of the fluid transportation device of the actuating and sensing module according to the embodiment of the present disclosure.

Please refer to FIGS. 2A, 2B, 2C and 2D, in which FIG. 2D depicts the actions of the fluid transportation device. The actuating and sensing module further comprises a substrate 15, which is a platform for integrating the sensor 11 with the fluid transportation device 13. For example, the substrate 15 is a printed circuit board (PCB). The sensor 11 and the fluid transportation device 13 are disposed on the substrate 15, after which the substrate 15 with the sensor 11 and the fluid transportation device 13 is disposed on an inner wall of the compartment 16 and/or the speaker enclosure 16a, 16b. It is noted that numerous modifications and alterations may be made while retaining the teachings of the invention. In a variant example, the substrate 15 is an application-specific integrated circuit (ASIC). In another variant example, the substrate 15 is a system on chip (SOC). The sensor 11 and the fluid transportation device 13 are disposed on the application-specific integrated circuit (ASIC) or the system on chip (SOC) and then the application-specific integrated circuit (ASIC) or the system on chip (SOC) is disposed on an inner wall of the compartment 16 and/or the speaker enclosure 16a, 16b.

Hereinafter, the actions of the fluid transportation device 13 will be described as follows. For example, the fluid transportation device 13 is a piezoelectric pump.

Figure 4A:
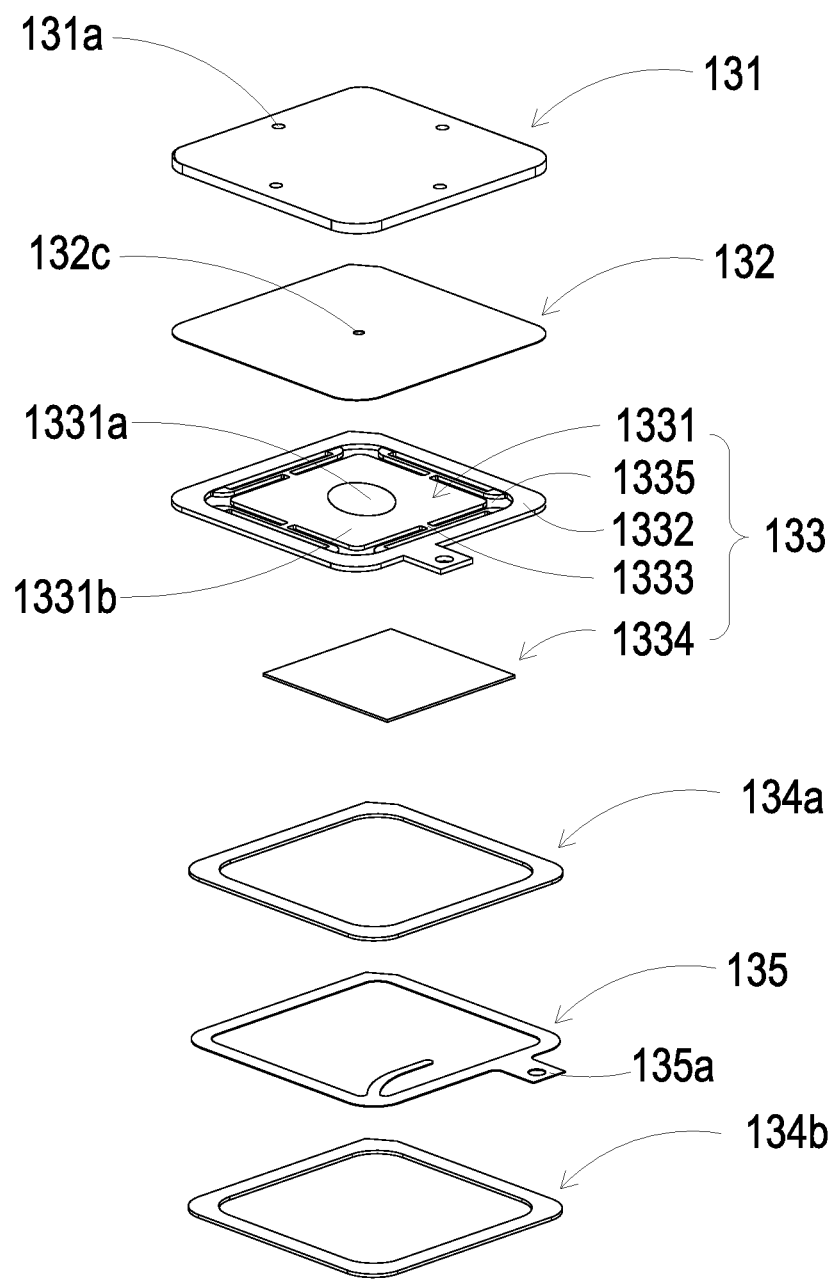
FIG. 4A is a schematic exploded view illustrating a fluid transportation device used in the electronic device of the present disclosure.
Figure 4B:
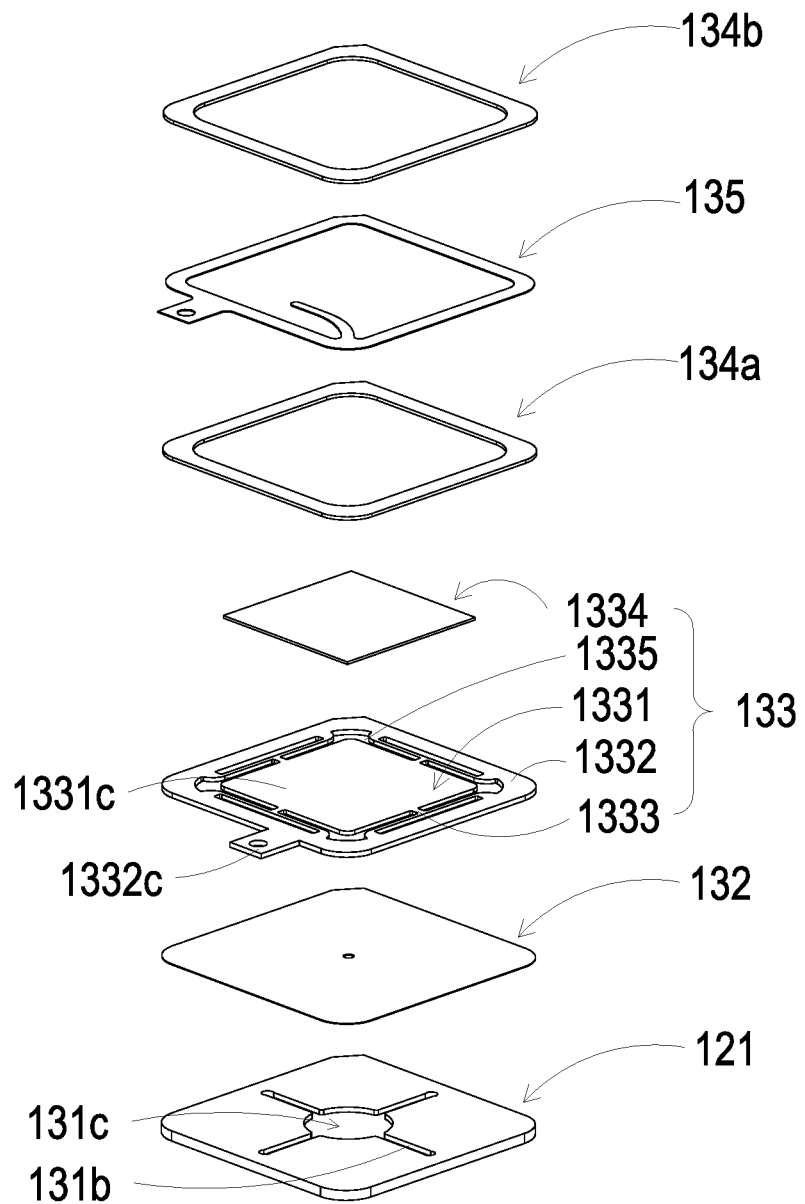
FIG. 4B is a schematic exploded view illustrating the fluid transportation device of FIG. 4A and taken along another viewpoint.
Figure 5:
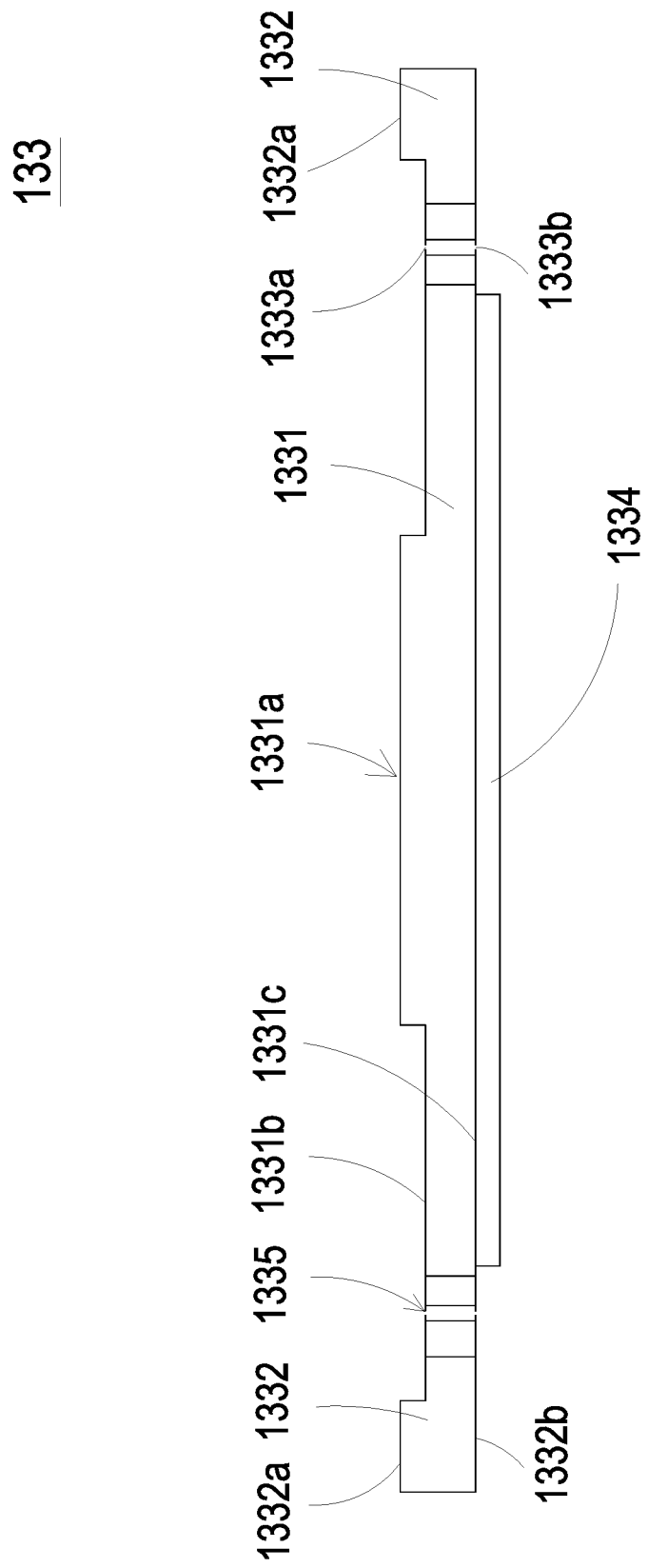
FIG. 5 is a schematic cross-sectional view illustrating the piezoelectric actuator of the fluid transportation device as shown in FIGS. 4A and 4B.
Figure 6:
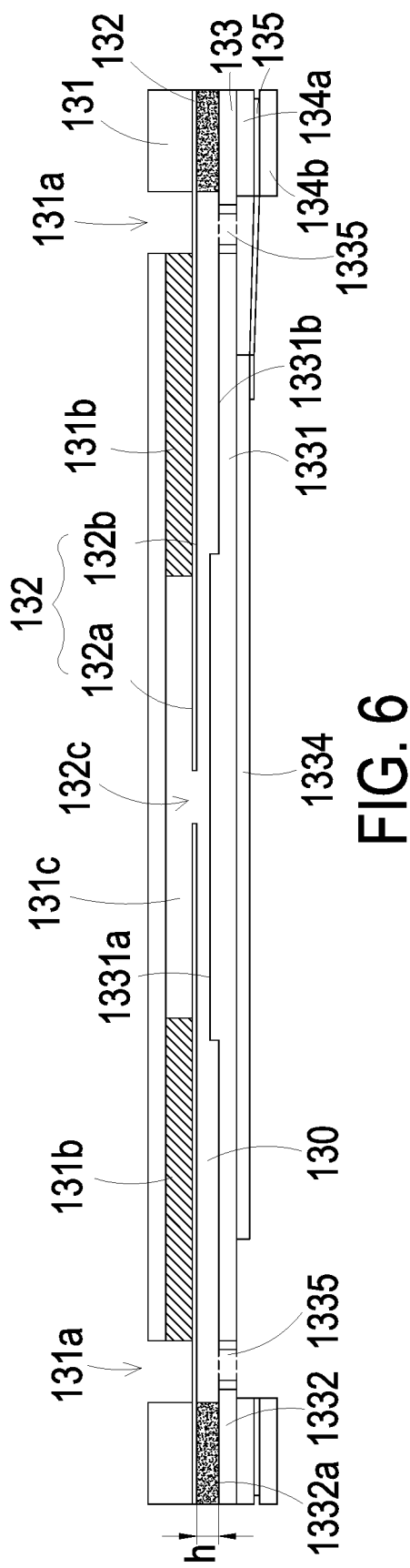
FIG. 6 is a schematic cross-sectional view illustrating the fluid transportation device as shown in FIGS. 4A and 4B.

FIG. 4A is a schematic exploded view illustrating a fluid transportation device used in the electronic device of the present disclosure. FIG. 4B is a schematic exploded view illustrating the fluid transportation device of FIG. 4A and taken along another viewpoint. FIG. 5 is a schematic cross-sectional view illustrating the piezoelectric actuator of the fluid transportation device as shown in FIGS. 4A and 4B. FIG. 6 is a schematic cross-sectional view illustrating the fluid transportation device as shown in FIGS. 4A and 4B.

The fluid transportation device 13 comprises a fluid inlet plate 131, a resonance plate 132, a piezoelectric actuator 133, a first insulation plate 134a, a conducting plate 135 and a second insulation plate 134b. The piezoelectric actuator 133 is aligned with the resonance plate 132. The fluid inlet plate 131, the resonance plate 132, the piezoelectric actuator 133, the first insulation plate 134a, the conducting plate 135 and the second insulation plate 134b are stacked on each other sequentially. After the above components are combined together, the cross-sectional view of the resulting structure of the fluid transportation device 13 is shown in FIG. 6.

The fluid inlet plate 131 comprises at least one inlet 131a. Preferably but not exclusively, the fluid inlet plate 131 comprises four inlets 131a. The inlets 131a run through the fluid inlet plate 131. In response to the action of the atmospheric pressure, the fluid can be introduced into the fluid transportation device 13 through the at least one inlet 131a. Moreover, at least one convergence channel 131b is formed on a first surface of the fluid inlet plate 131, and is in communication with the at least one inlet 131a on a second surface of the fluid inlet plate 131. Moreover, a central cavity 131c is located at the intersection of the convergence channels 131b. The central cavity 131c is in communication with the at least one convergence channel 131b, such that the fluid entered by the at least one inlet 131a would be introduced into the at least one convergence channel 131b and is guided to the central cavity 131c. In this embodiment, the at least one inlet 131a, the at least one convergence channel 131b and the central cavity 131c of the fluid inlet plate 131 are integrally formed. The central cavity 131c forms a convergence chamber for temporarily storing the fluid. Preferably but not exclusively, the fluid inlet plate 131 is made of stainless steel. Moreover, the depth of the convergence chamber defined by the central cavity 131c may be equal to the depth of the at least one convergence channel 131b. The resonance plate 132 is made of a flexible material, which is preferably but not exclusively copper. The resonance plate 132 comprises a central aperture 132c aligned with the central cavity 131c of the fluid inlet plate 131 which allows the fluid to be transferred therethrough.

The piezoelectric actuator 133 comprises a suspension plate 1331, an outer frame 1332, at least one bracket 1333 and a piezoelectric plate 1334. The piezoelectric plate 1334 is attached on a first surface 1331c of the suspension plate 1331. In response to an applied voltage, the piezoelectric plate 1334 is subjected to a deformation. When the piezoelectric plate 1334 is subjected to the deformation, the suspension plate 1331 is subjected to a bending vibration. The at least one bracket 1333 is connected between the suspension plate 1331 and the outer frame 1332, while the two ends of the bracket 1333 are connected with the outer frame 1332 and the suspension plate 1331 respectively that the bracket 1333 can elastically support the suspension plate 1331. At least one vacant space 1335 is formed between the bracket 1333, the suspension plate 1331 and the outer frame 1332. The at least one vacant space 1335 is in communication with a fluid channel 19 (see FIGS. 2A to 2D) for allowing the fluid to go through. The type of the suspension plate 1331 and the outer frame 1332 and the type and the number of the at least one bracket 1333 may be varied according to the practical requirements. The outer frame 1332 is arranged around the suspension plate 1331. Moreover, a conducting pin 1332c is protruded outwardly from the outer frame 1332 so as to be electrically connected with an external circuit (not shown).

As shown in FIG. 5, the suspension plate 1331 has a bulge 1331a that makes the suspension plate 1331 a stepped structure. The bulge 1331a is formed on a second surface 1331b of the suspension plate 1331. The bulge 1331a may be a circular convex structure. A top surface of the bulge 1331a of the suspension plate 1331 is coplanar with a second surface 1332a of the outer frame 1332, while the second surface 1331b of the suspension plate 1331 is coplanar with a second surface 1333a of the bracket 1333. Moreover, there is a drop of specified amount from the bulge 1331a of the suspension plate 1331 (or the second surface 1332a of the outer frame 1332) to the second surface 1331b of the suspension plate 1331 (or the second surface 1333a of the bracket 1333). A first surface 1331c of the suspension plate 1331, a first surface 1332b of the outer frame 1332 and a first surface 1333b of the bracket 1333 are coplanar with each other. The piezoelectric plate 1334 is attached on the first surface 1331c of the suspension plate 1331. In some other embodiments, the suspension plate 1331 may be a square plate structure with two flat surfaces but the type of the suspension plate 1331 may be varied according to the practical requirements. In this embodiment, the suspension plate 1331, the at least bracket 1333 and the outer frame 1332 are integrally formed and produced by using a metal plate (e.g., a stainless steel plate). In an embodiment, the length of a side of the piezoelectric plate 1334 is smaller than the length of a side of the suspension plate 1331. In another embodiment, the length of a side of the piezoelectric plate 1334 is equal to the length of a side of the suspension plate 1331. Similarly, the piezoelectric plate 1334 is a square plate structure corresponding to the suspension plate 1331.

In the fluid transportation device 13, the first insulation plate 134a, the conducting plate 135 and the second insulation plate 134b are stacked on each other sequentially and located under the piezoelectric actuator 133. The profiles of the first insulation plate 134a, the conducting plate 135 and the second insulation plate 134b substantially match the profile of the outer frame 1332 of the piezoelectric actuator 133. The first insulation plate 134a and the second insulation plate 134b are made of an insulating material (e.g. a plastic material) for providing insulating efficacy. The conducting plate 135 is made of an electrically conductive material (e.g. a metallic material) for providing electrically conducting efficacy. Moreover, the conducting plate 135 has a conducting pin 135a so as to be electrically connected with an external circuit (not shown).

Please refer to FIG. 6. In an embodiment, the fluid inlet plate 131, the resonance plate 132, the piezoelectric actuator 133, the first insulation plate 134a, the conducting plate 135 and the second insulation plate 134b of the fluid transportation device 13 are stacked on each other sequentially. Moreover, there is a gap h between the resonance plate 132 and the outer frame 1332 of the piezoelectric actuator 133, which is formed and maintained by a filler (e.g. a conductive adhesive) inserted therein in this embodiment. The gap h ensures the proper distance between the resonance plate 132 and the bulge 1331a of the suspension plate 1331 of the piezoelectric actuator 133, so that the fluid can be transferred quickly, the contact interference is reduced and the generated noise is largely reduced. In some embodiments, the height of the outer frame 1332 of the piezoelectric actuator 133 is increased, so that the gap is formed between the resonance plate 132 and the piezoelectric actuator 133.

Please refer to FIG. 4A, FIG. 4B and FIG. 6. After the fluid inlet plate 131, the resonance plate 132 and the piezoelectric actuator 133 are combined together, a movable part 132a and a fixed part 132b of the resonance plate 132 are defined. The movable part 132a is around the central aperture 132c. A convergence chamber for converging the fluid is defined by the movable part 132a of the resonance plate 132 and the fluid inlet plate 131 collaboratively. Moreover, a first chamber 130 is formed between the resonance plate 132 and the piezoelectric actuator 133 for temporarily storing the fluid. Through the central aperture 132c of the resonance plate 132, the first chamber 130 is in communication with the central cavity 131c of the fluid inlet plate 131. The peripheral regions of the first chamber 130 are in communication with the fluid channel 19 through the vacant space 1335 between the brackets 1333 of the piezoelectric actuator 133.

FIGS. 7A to 7E schematically illustrate the actions of the fluid transportation device of the electronic device according to the embodiment of the present disclosure. Please refer to FIG. 4A, FIG. 4B, FIG. 6 and FIGS. 7A to 7E. The actions of the fluid transportation device will be described as follows. When the fluid transportation device 13 is enabled, the piezoelectric actuator 133 is vibrated along a vertical direction in a reciprocating manner by using the bracket 1333 as a fulcrum. Since the resonance plate 132 is light and thin, when the piezoelectric actuator 133 is vibrated downwardly in response to the applied voltage, the resonance plate 132 is vibrated along the vertical direction in the reciprocating manner because of the resonance of the piezoelectric actuator 133. More especially, the region of the resonance plate 132 corresponding to the central cavity 131c of the fluid inlet plate 131 is also subjected to a curvy deformation. The region of the resonance plate 132 corresponding to the central cavity 131c of the fluid inlet plate 131 is the movable part 132a of the resonance plate 132. When the piezoelectric actuator 133 is vibrated downwardly, the movable part 132a of the resonance plate 132 is subjected to the curvy deformation because the movable part 132a of the resonance plate 132 is pushed by the fluid and vibrated in response to the piezoelectric actuator 133. In response to the downward vibration of the piezoelectric actuator 133, the fluid is fed into the at least one inlet 131a of the fluid inlet plate 131. Then, the fluid is transferred to the central cavity 131c of the fluid inlet plate 131 through the at least one convergence channel 131b. Then, the fluid is transferred through the central aperture 132c of the resonance plate 132 corresponding to the central cavity 131c, and introduced downwardly into the first chamber 130. As the piezoelectric actuator 133 is enabled, the resonance of the resonance plate 132 occurs. Consequently, the resonance plate 132 is also vibrated along the vertical direction in the reciprocating manner.

Figure 7A:
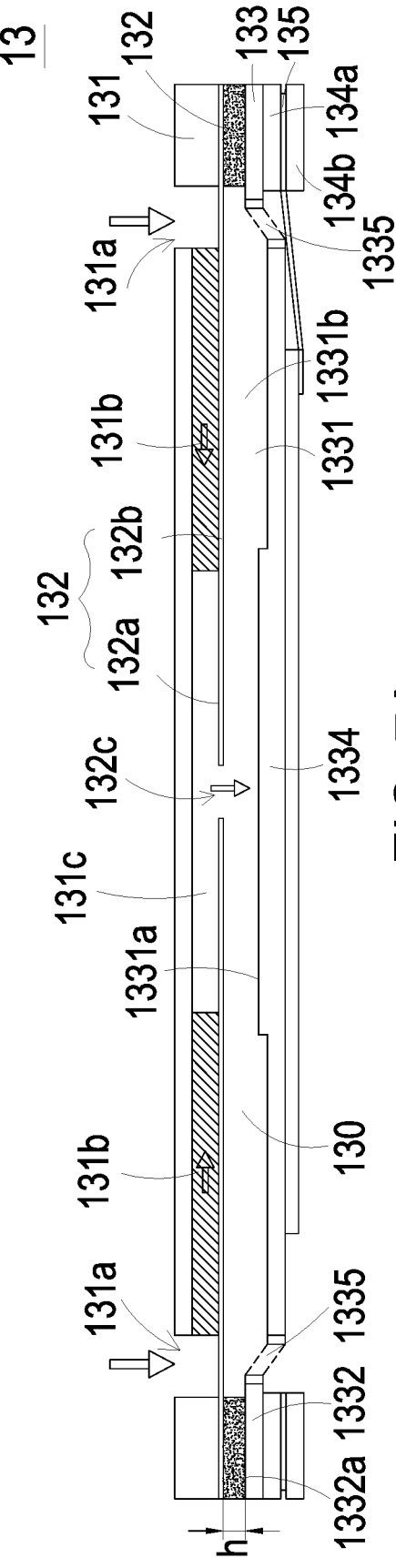
FIGS. 7A to 7E schematically illustrate the actions of the fluid transportation device of the electronic device according to the embodiment of the present disclosure.
Figure 7B:
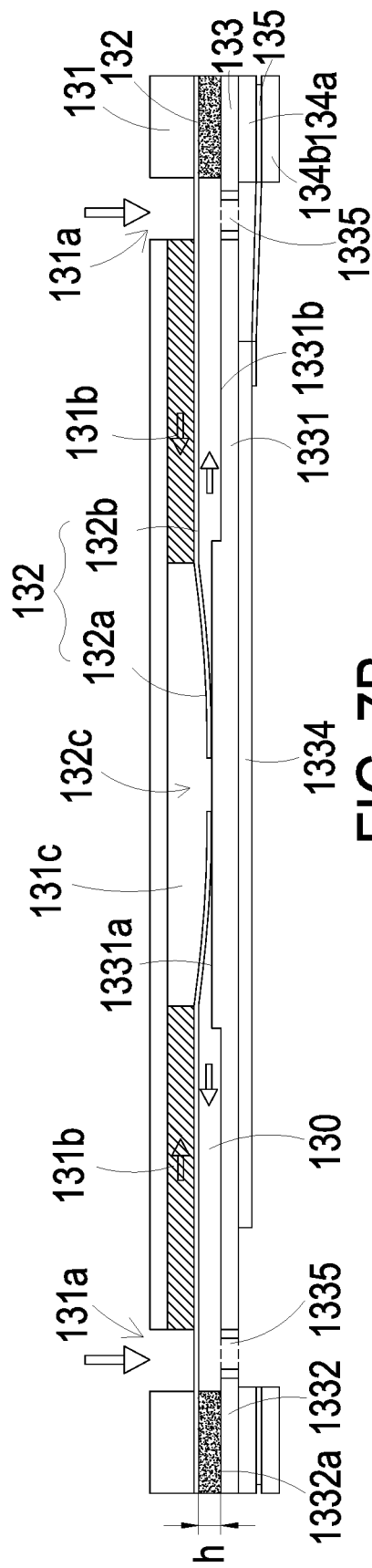

As shown in FIG. 7B, during the vibration of the movable part 132a of the resonance plate 132, the movable part 132a moves down till bring contacted with the bulge 1331a of the suspension plate 1331 of the piezoelectric actuator 133. The region of the resonance plate 132 excluding the movable part 132a is the fixed part 132b. Meanwhile, the gap of the convergence chamber between the bulge 1331a of the suspension plate 1331 and the fixed part 132b of the resonance plate 132 is not reduced. Due to the deformation of the resonance plate 132, the volume of the first chamber 130 is shrunken and a middle communication space of the first chamber 130 is closed. Under this circumstance, the pressure gradient occurs to push the fluid in the first chamber 130 moving toward peripheral regions of the first chamber 130 and flowing downwardly through the vacant space 1335 of the piezoelectric actuator 133.

Figure 7C:
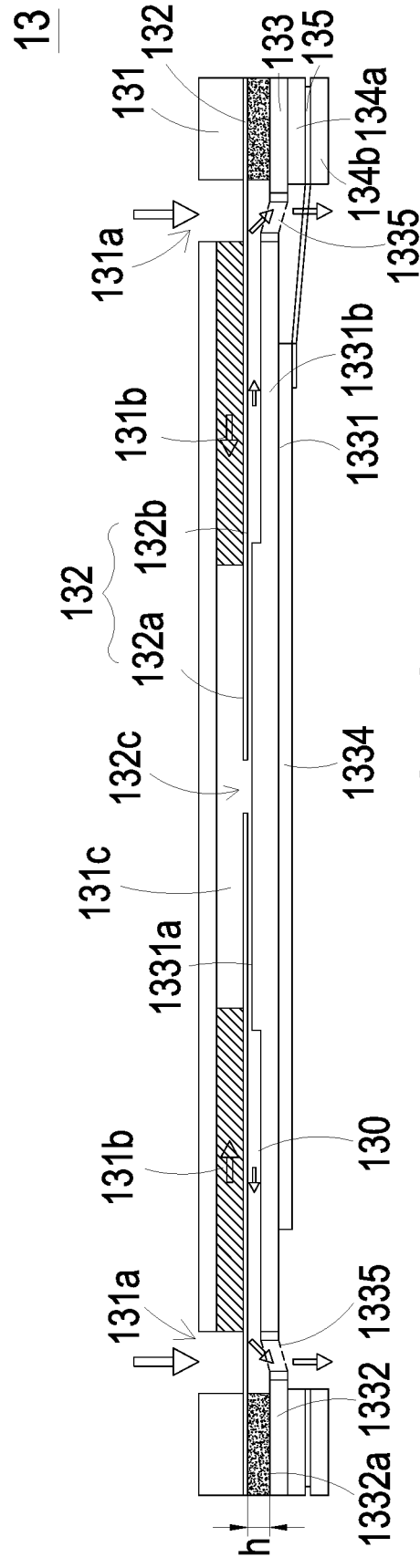

As shown in FIG. 7C, the movable part 132a of the resonance plate 132 has returned to its original position when the piezoelectric actuator 133 has ascended at a vibration displacement to an upward position. Consequently, the volume of the first chamber 130 is consecutively shrunken that generating the pressure gradient which makes the fluid in the first chamber 130 continuously pushed toward peripheral regions. Meanwhile, the fluid is continuously fed into the at least one inlet 131a of the fluid inlet plate 131, and transferred to the central cavity 131c.

Figure 7D:
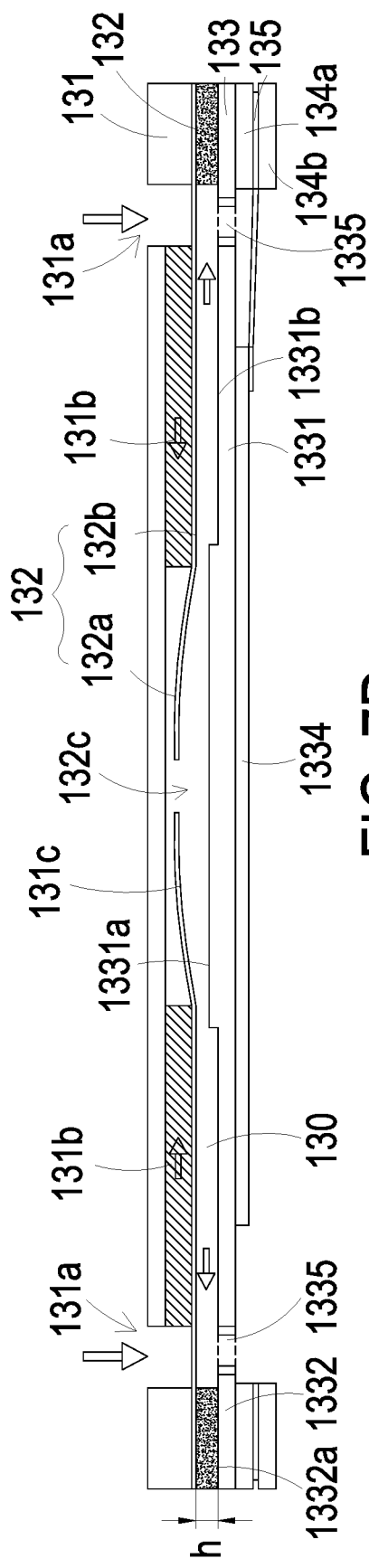

Then, as shown in FIG. 7D, the resonance plate 132 moves upwardly, which is cause by the resonance of the upward motion of the piezoelectric actuator 133. That is, the movable part 132a of the resonance plate 132 is also vibrated upwardly. Consequently, the fluid is slowly fed into the at least one inlet 131a of the fluid inlet plate 131, and transferred to the central cavity 131c.

Figure 7E:
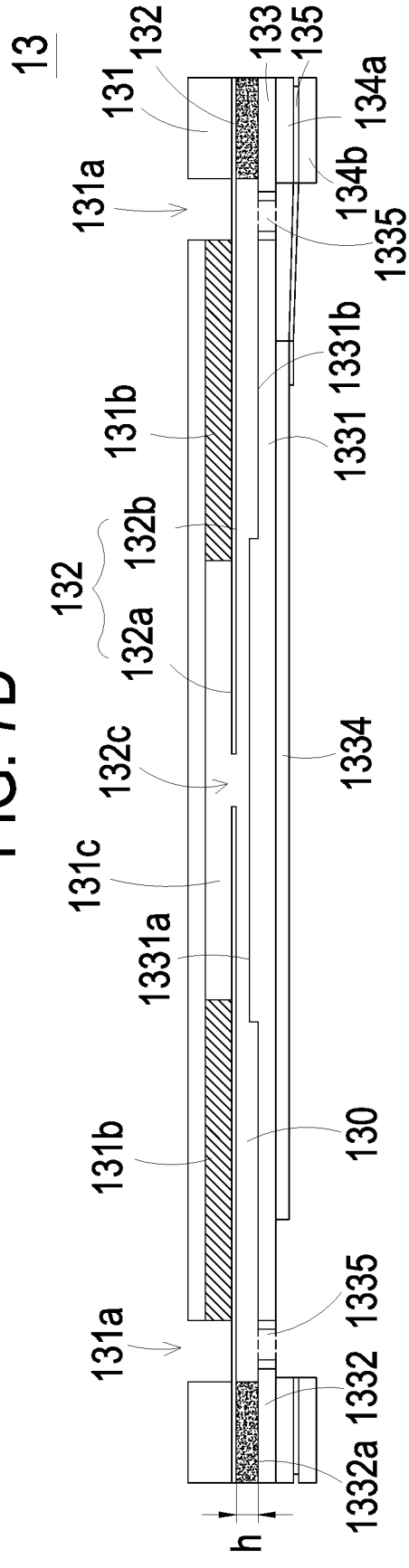

As shown in FIG. 7E, the movable part 132a of the resonance plate 132 has returned to its original position. When the resonance plate 132 is vibrated along the vertical direction in the reciprocating manner, the gap h between the resonance plate 132 and the piezoelectric actuator 133 is helpful to increase the amplitude of vibration of the resonance plate 132. That is, the thickness of the gap h between the resonance plate 132 and the piezoelectric actuator 133 affects the amplitude of vibration of the resonance plate 132. Consequently, a pressure gradient is generated in the fluid channels of the fluid transportation device 13 to facilitate the fluid to flow at a high speed. Moreover, since there is an impedance difference between the feeding direction and the exiting direction, the fluid can be transmitted from the inlet side to the outlet side. Moreover, even if the outlet side has a gas pressure, the fluid transportation device 13 still has the capability of pushing the fluid to the fluid channel 19 while achieving the silent efficacy.

The steps of FIGS. 7A to 7E are repeatedly done. Consequently, fluid circulation is generated in which the ambient fluid is transferred from the outside to the inside by the fluid transportation device 13.

Please refer to FIG. 2D again. After the fluid inlet plate 131, the resonance plate 132, the piezoelectric actuator 133, the first insulation plate 134a, the conducting plate 135 and the second insulation plate 134b are sequentially stacked, the fluid transportation device 13 is assembled. After the fluid transportation device 13 and the sensor 11 are disposed on the substrate 15, the actuating and sensing module is assembled, in which the fluid channel 19 is arranged between the fluid transportation device 13 and the substrate 15. As so, the actuating and sensing module is disposed on the inner wall of the compartment 16 or the speaker compartment 16a, 16b. During operation of the fluid transportation device 13, the fluid is pumped and introduced into the compartment 16 through the opening 121 of the electronic device 10, then being transferred through the channel 19 along the direction indicated by the arrow (see FIG. 2D), by which the fluid is directly guided to the sensor 11 at a stable flowrate. Consequently, the sensor 11 can monitor the fluid guided in the compartment 16 and acquire the accurate sensing results. Moreover, the response time of the sensor 11 is reduced.

From the above descriptions, the present disclosure provides an electronic device with an actuating and sensing module. The actuating and sensing module is a modular structure of a sensor and a fluid transportation device. The sensor is disposed within a speaker enclosure of the electronic device and is capable of directly monitoring the fluid in the environment of the electronic device of the present disclosure. The speaker enclosure is divided into a first speaker compartment and a second speaker compartment by a partition plate. The fluid is pumped and introduced into the first speaker compartment of the speaker enclosure and guided to the sensor by the fluid transportation device at a stable flowrate. Since the fluid is guided to the sensor at the stable flowrate, the sensor can monitor the fluid to acquire the accurate sensing results. Moreover, since the response time of the sensor is reduced, the efficiency of monitoring the fluid is enhanced. Since the speaker is accommodated within the second speaker compartment of the speaker enclosure, the sound quality of the speaker is not interfered by the sensor and the fluid transportation device. Since the sensor is protected by the casing of the electronic device, the sensor is not readily collided by the foreign matter and suffered from damage. Moreover, since the sensing result of the sensor is not interfered by the fluid and the temperature within the electronic device, the accuracy of the sensor is enhanced. In other words, the electronic device of the present disclosure is industrially valuable.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An electronic device, comprising:
a casing having an opening;
a speaker enclosure disposed within the casing to enclose a speaker, the speaker enclosure being in communication with the opening of the casing and divided into a first speaker compartment and a second speaker compartment by a partition plate disposed corresponding to the opening of the casing, so that the opening of the casing is in communication with the first speaker compartment and the second speaker compartment respectively; and
at least one actuating and sensing module disposed within the first speaker compartment, the speaker being disposed within the second speaker compartment, the actuating and sensing module comprising a fluid transportation device, a sensor and a substrate, wherein the sensor is arranged adjacent to the fluid transportation device, and the sensor and the fluid transportation device are disposed on a same surface of the substrate, and a fluid channel is arranged between the fluid transportation device and the substrate, wherein the fluid transportation device is driven to transport a fluid from outside the casing into the first speaker compartment through the opening of the casing, so that the fluid is transported to the sensor through the fluid channel by the fluid transportation device and sensed by the sensor.

2. The electronic device according to claim 1, wherein the fluid is a gas.

3. The electronic device according to claim 1, wherein the fluid is a liquid.

4. The electronic device according to claim 1, wherein the speaker enclosure is separated and independent from an inner space of the electronic device.

5. The electronic device according to claim 1, wherein before the sensor and the fluid transportation device are disposed within the first speaker compartment, the sensor and the fluid transportation device are integrated into an application-specific integrated circuit.

6. The electronic device according to claim 1, wherein before the sensor and the fluid transportation device are disposed within the first speaker compartment, the sensor and the fluid transportation device are packaged on a system on chip.

7. The electronic device according to claim 1, wherein the sensor comprises a gas sensor.

8. The electronic device according to claim 1, wherein the sensor comprises a liquid sensor.

9. The electronic device according to claim 1, wherein the sensor comprises an ozone sensor.

10. The electronic device according to claim 1, wherein the sensor comprises a particulate sensor.

11. The electronic device according to claim 1, wherein the sensor comprises a volatile organic compound sensor.

12. The electronic device according to claim 1, wherein the sensor comprises a light sensor.

13. The electronic device according to claim 1, wherein the sensor comprises at least one selected from the group consisting of an oxygen sensor, a carbon monoxide sensor, a carbon dioxide sensor, a temperature sensor, a liquid sensor and a humidity sensor.

14. The electronic device according to claim 1, wherein the fluid transportation device is a MEMS pump.

15. The electronic device according to claim 1, wherein the fluid transportation device is a piezoelectric pump.

16. The electronic device according to claim 15, wherein the fluid transportation device comprises:
a fluid inlet plate having at least one inlet for introducing the fluid, at least one convergence channel disposed corresponding to the at least one inlet, and a central cavity forming a convergence chamber, wherein the at least one convergence channel guides the fluid introduced from the at least one inlet into the convergence chamber so that the fluid is converged;
a resonance plate having a central aperture aligned with the convergence chamber, the resonance plate comprising a movable part around the central aperture; and
a piezoelectric actuator facing the resonance plate, wherein a gap is formed between the resonance plate and the piezoelectric actuator to define a first chamber, wherein when the piezoelectric actuator is enabled, the fluid is fed into the fluid transportation device through the at least one inlet of the fluid inlet plate, converged to the central cavity through the at least one convergence channel, transferred through the central aperture of the resonance plate, and introduced into the first chamber, wherein the fluid is transferred through a resonance between the piezoelectric actuator and the movable part of the resonance plate.

17. The electronic device according to claim 16, wherein the piezoelectric actuator comprises:
a suspension plate having a first surface and an opposing second surface, wherein the suspension plate is permitted to undergo a bending vibration;
an outer frame arranged around the suspension plate;
at least one bracket connected between the suspension plate and the outer frame for elastically supporting the suspension plate; and
a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

18. The electronic device according to claim 17, wherein the suspension plate is a square suspension plate with a bulge.

19. The electronic device according to claim 16, wherein the fluid transportation device further comprises a conducting plate, a first insulation plate and a second insulation plate, wherein the fluid inlet plate, the resonance plate, the first insulation plate, the conducting plate and the second insulation plate are sequentially stacked.

20. An electronic device, comprising:
at least one casing having at least one opening;
at least one speaker enclosure being in communication with the at least one opening of the at least one casing and divided into at least one first speaker compartment and at least one second speaker compartment by at least one partition plate disposed corresponding to the at least one opening of the at least one casing, so that the at least one opening off the at least one casing is in communication with the at least one first speaker compartment and the at least one second speaker compartment respectively; and
at least one actuating and sensing module disposed within the at least one first speaker compartment, the at least one speaker being disposed within the at least one second speaker compartment, the at least one actuating and sensing module comprising at least one fluid transportation device, at least one sensor and at least one substrate, wherein the at least one sensor is arranged adjacent to the at least one fluid transportation device, and the at least one sensor and the at least one fluid transportation device are disposed on a same surface of the at least one substrate, and at least one fluid channel is arranged between the at least one fluid transportation device and the at least one substrate, wherein the at least one fluid transportation device is driven to transport at least one fluid from outside the at least one casing into the at least one first speaker compartment through the at least one opening of the at least one casing, so that the at least one fluid is transported to the at least one sensor through the at least one fluid channel by the at least one fluid transportation device and sensed by the at least one sensor.

* * * * *